US010980901B2

(12) United States Patent
Morgenstern et al.

(10) Patent No.: US 10,980,901 B2
(45) Date of Patent: Apr. 20, 2021

(54) TREATMENT OF PMSA EXPRESSING CANCERS

(71) Applicants: THE EUROPEAN ATOMIC ENERGY COMMUNITY (EURATOM), REPRESENTED BY THE EUROPEAN COMMISSION, Brussels (BE); UNIVERSITÄT HEIDELBERG, Heidelberg (DE)

(72) Inventors: Alfred Morgenstern, Karlsruhe (DE); Frank Bruchertseifer, Stutensee (DE); Christos Apostolidis, Heidelberg (DE); Uwe Haberkorn, Schwetzingen (DE); Frederik Giesel, Heidelberg (DE); Clemens Kratochwil, Hirschberg a.d.B. (DE)

(73) Assignees: The European Atomic Energy Community (EURATOM), Represented by the European Commission, Brussels (BE); Universität Heidelberg, Heidelberg (DE)

( * ) Notice: Subject to any disclaimer, the term of this patent is extended or adjusted under 35 U.S.C. 154(b) by 0 days.

(21) Appl. No.: 16/470,104

(22) PCT Filed: Dec. 15, 2016

(86) PCT No.: PCT/EP2016/081313
§ 371 (c)(1),
(2) Date: Jun. 14, 2019

(87) PCT Pub. No.: WO2018/108287
PCT Pub. Date: Jun. 21, 2018

(65) Prior Publication Data
US 2020/0016281 A1    Jan. 16, 2020

(51) Int. Cl.
*A61K 51/04*       (2006.01)
*A61K 49/00*       (2006.01)
*A61P 35/04*       (2006.01)

(52) U.S. Cl.
CPC ...... *A61K 51/0482* (2013.01); *A61K 51/0497* (2013.01); *A61P 35/04* (2018.01)

(58) Field of Classification Search
CPC .................. A61K 49/00; A61K 51/04
See application file for complete search history.

(56) References Cited

U.S. PATENT DOCUMENTS

| 8,926,944  | B2 * | 1/2015  | Babich | ................ | C07F 5/003 |
|            |      |         |        |                  | 424/1.65   |
| 10,398,791 | B2 * | 9/2019  | Eder   | ................ | A61K 51/0497 |
| 10,471,160 | B2 * | 11/2019 | Eder   | ................ | A61K 51/0402 |

OTHER PUBLICATIONS

Apostolidis Christos, et al., "Production of Ac-225 from Th-229 for targeted alpha therapy", Analytical Chemistry, 2005;77(19):6288-91.
Hadaschik Boris, "Re:225Ac-PSMA-617 for PSMA-Targeting Alpharadiation Therapy of Patients with Metastatic Castration-resistant Prostate Cancer", European Urology, Aug. 21, 2016, vol. 70, Issue 6, pp. 1080-1081.
Zielinska B. et al., "An Improved Method for the Production of Ac225/Bi-213 from Th-229 for Targeted Alpha Therapy", Solvent Extraction and Ion Exchange, 2007;25(3):339-49.
Kratochwil, Clemens et al., "225 Ac-PSMA-617 for PSMA-Targeted α-Radiation Therapy of Metastatic Castration-Resistant Prostate Cancer", The Journal of Nuclear Medicine, Jul. 7, 2016, vol. 57, No. 12, pp. 1941-1944.
Sathekge, Mike et al., "$^{68}$Ga-PSMA-HBED-CC PET imaging in breast carcinoma patients", European Journal of Nuclear Medicine and Molecular Imaging, Nov. 8, 2016, vol. 44, pp. 689-694.
Kratochwil, Clemens et al., "Ac-225-DOTATOC—an empiric dose finding for alpha particle emitter based radionuclide therapy of neuroendocrine tumors", The Journal of Nuclear Medicine, May 1, 2015, vol. 56, No. Supplement 3, p. 1232.
Afshar-Oromieh, Ali et al., "The Rise of PSMA Ligands for Diagnosis and Therapy of Prostate Cancer", The Journal of Nuclear Medicine, Oct. 2016, vol. 57, No. Suppl. 3, pp. 79S-89S.
International Search Report and Written Opinion for corresponding International Application No. PCT/EP2016/081313, dated Sep. 7, 2017 (9 pgs.).

* cited by examiner

Primary Examiner — Jake M Vu
Assistant Examiner — Jagadishwar R Samala
(74) Attorney, Agent, or Firm — Lewis Roca Rothgerber Christie LLP

(57) ABSTRACT

The invention relates to a method for treating PSMA expressing cancers, wherein the method comprises administering to patient in need thereof an effective amount of one or more Ac-225-radiopharmaceuticals, wherein the effective amount of said one or more Ac-225-radiopharmaceuticals is administered as a dosage of from 25 kBq to 400 kBq/kg of body weight of said patient or wherein the effective amount of said one or more Ac-225-radiopharmaceuticals is administered as a unitary dosage of from 3 MBq to 30 MBq to said patient.

13 Claims, 8 Drawing Sheets

A          B

A

B

A

B

TREATMENT OF PMSA EXPRESSING CANCERS

CROSS REFERENCE TO RELATED APPLICATIONS

This application is a National Phase patent application of International Patent Application Number PCT/EP2016/081313, filed on Dec. 15, 2016, the contents of which are incorporated herein by reference.

TECHNICAL FIELD

The invention generally relates to radiopharmaceuticals for treating cancer, i.e. molecules labelled with radionuclides able to target certain cancer cells, in particular PSMA expressing cancer cells.

BACKGROUND ART

In fact, radiopharmaceuticals are particularly interesting as tracers, imaging agents and for treating various cancers. Radiopharmaceuticals generally comprise a targeting (ligand) moiety and chelating moiety, the former being specific to certain target markers (predominantly) expressed by target cells and the latter being able to chelate (bind) a radionuclide. The so-formed radiopharmaceutical is thus able to target and bind to the desired site of such cells and it may be traced, be used for imaging or may act locally by destroying the cell to which it is bound or nearby cells, such as cancerous cells.

There are many different cancers and thus even more potentially useful different targeting sites for appropriately conceived radiopharmaceuticals. So, even for a given cancer type a number of targeting sites may be considered and may (or may not) be of use for the docking of radiopharmaceuticals.

Hence, choosing an appropriate targeting site and developing an appropriate targeting moiety combined to the identification of an appropriate chelating unit with an appropriate radionuclide to a working radiopharmaceutical is a challenging, yet promising way to be able to manage tumors.

Among cancers, PSMA (Prostate Specific Membrane Antigen) expressing cancers, notably prostate and breast cancers indubitably rank among the most frequent cancers. However, in spite of the considerable efforts spent in various medical approaches during the last decades to find efficient treatment methods, these cancers still are among those for which a reliable and efficient therapy is highly desirable.

Technical Problem

It is an object of the present invention to provide a method for treating PSMA expressing cancers. The method should allow for even treating patients refractory to established therapies. Furthermore, the devised method should allow for an efficient treatment of the cancer, while having as few side-effects as possible.

General Description of the Invention

In order to overcome the above-mentioned problems, the present invention provides in a first aspect a method for treating PSMA expressing cancers or cancer cells, wherein the method comprises administering to patient in need thereof an effective amount of one or more Ac-225-radiopharmaceuticals, said one or more Ac-225-radiopharmaceuticals comprising Ac-225 chelated with a targeting compound of Formula (A), (B), (C), (D) or (E):

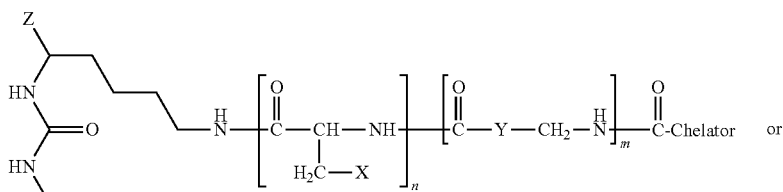

Formula (A)

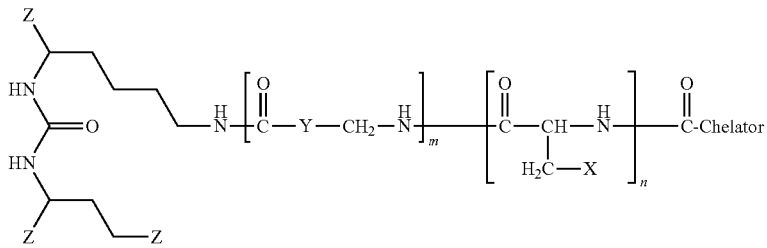

Formula (B)

with:
n: 0, 1
m: 1, 2, 3, 4
Z: —CO$_2$H, —SO$_2$H, —SO$_3$H, —SO$_4$H, —PO$_2$H, —PO$_3$H, —PO$_4$H$_2$
X: naphthyl, phenyl, biphenyl, indolyl (=2,3-benzopyrrolyl), benzothiazolyl
Y: aryl, alkylaryl, cyclopentyl, cyclohexyl, cycloheptyl
Chelator: 1,4,7,10-tetraazacyclododecane-N,N',N",N"'-tetraacetic acid (DOTA), N,N"-bis[2-hydroxy-5-(carboxyethyl)benzyl]ethylenediamine-N,N"-diacetic acid (HBED-CC),
1,4,7-triazacyclononane-1,4,7-triacetic acid (=NOTA),
2-(4,7-bis(carboxymethyl)-1,4,7-triazonan-1-Opentanedioic acid (NODAGA),
2-(4,7,10-tris(carboxymethyl)-1,4,7,10-tetraazacyclododecan-1-yl)pentanedioic acid (DOTAGA), 1,4,7-triazacyclononane phosphinic acid (TRAP),
1,4,7-triazacyclononane-1-[methyl(2-carboxyethyl)phosphinic acid]-4,7-bis[methyl(2-hydroxymethyl)phosphinic acid] (NOPO),
3,6,9,15-tetraazabicyclo[9.3.1.]pentadeca-1(15), 11,13-triene-3,6,9-triacetic acid (PCTA),
N'-{5-[Acetyl(hydroxy)amino]pentyl}-N-[5-({4-[(5-aminopentyl)-(hydroxy)amino]-4-oxobutanoyl}amino)pentyl]-N-hydroxysuccinamide (DFO),
diethylenetriaminepentaacetic acid (DTPA),
trans-cyclohexyl-diethylenetriaminepentaacetic acid (CHX-DTPA),
1-oxa-4,7,10-triazacyclododecane-4,7,10-triacetic acid (oxo-Do3A) p-isothiocyanatobenzyl-DTPA (SCN-Bz-DTPA),
1-(p-isothiocyanatobenzyl)-3-methyl-DTPA (1B3M),
2-(p-isothiocyanatobenzyl)-4-methyl-DTPA (1M3B), or
1-(2)-methyl-4-isocyanatobenzyl-DTPA (MX-DTPA);

erably 6 to 10 carbon atoms. The aryl group can be substituted, where appropriate, with one or several ring substituents, like alkyl groups. Preferred aryl groups are phenyl, benzyl or naphthyl.

Although it is preferred that the Z group is —$CO_2H$ it may be easily replaced with biosteric replacements such as —$SO_2H$, —$SO_3H$, —$SO_4H$, —$PO_2H$, —$PO_3H$, —$PO_4H_2$.

The term "minibody" refers to an optionally engineered fragment of an (entire) antibody. Hence, a PSMA minibody (also called anti-PSMA minibody) is a fragment of a PSMA antibody (also called anti-PSMA antibody) which may be obtained in the same way as the antibody itself, i.e. by extraction from biological culture systems (cell cultures, egg, hamsters, mice, etc.) or they may be engineered. Engineered antibody fragments generally offer faster delivery with retained tumor specificity and rapid clearance from non-tumor tissues compared to the corresponding (entire) antibody. Appropriate PSMA antibodies and PSMA mini-

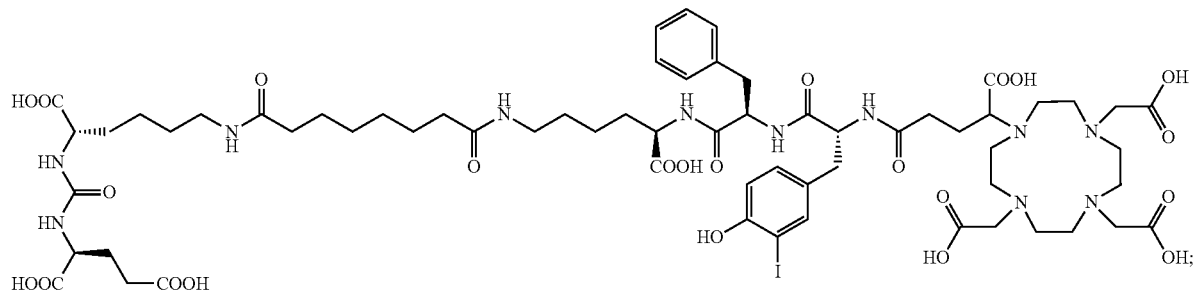

Formula (C)

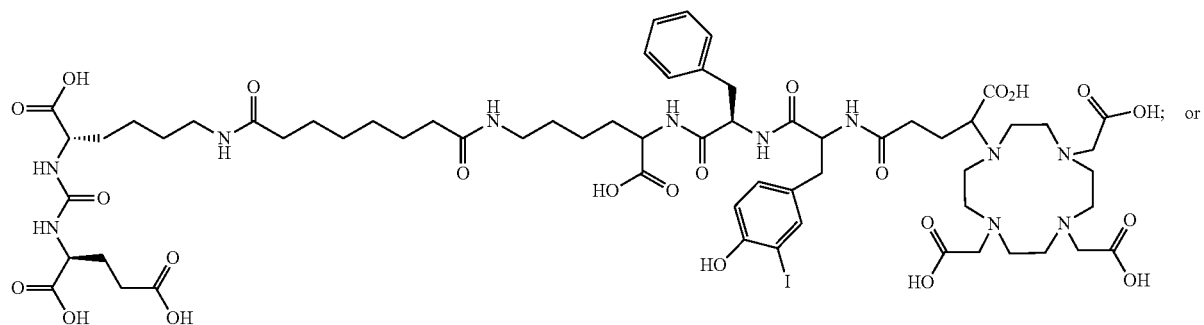

Formula (D)

(PSMA antibody)-Chelator or (PSMA minibody)-Chelator.

Formula (E)

The "alkyl" residue preferably has 1 to 10 carbon atoms and can be linear or branched, unsubstituted or substituted. Preferred alkyl residues are methyl, ethyl, n-propyl, iso-propyl, n-butyl, tert-butyl, n-pentanyl, n-hexanyl. The same also applies to the corresponding cycloalkyl residues having preferably 3 to 10 carbon atoms.

The term "aryl" refers to an aromatic monocyclic or polycyclic ring system having 6 to 14 carbon atoms, prefbodies are e.g. antibody J591 and corresponding minibody IAB2M, GCP-05, 1H8H5, SP29, FOLH1, etc. Compounds of Formula (E) comprise a chelating moiety capable of chelating Ac-225. Appropriate chelating moieties are e.g. those mentioned for compounds of Formula (A) and (B), but other chelators may be used. A particularly preferred compound of Formula (E) is e.g. Df-IAB2M, Df being desferrioxamine.

Thus, preferred targeting compounds comprised within the Ac-225-radiopharmaceuticals useable according to the present invention are selected for example among the following:
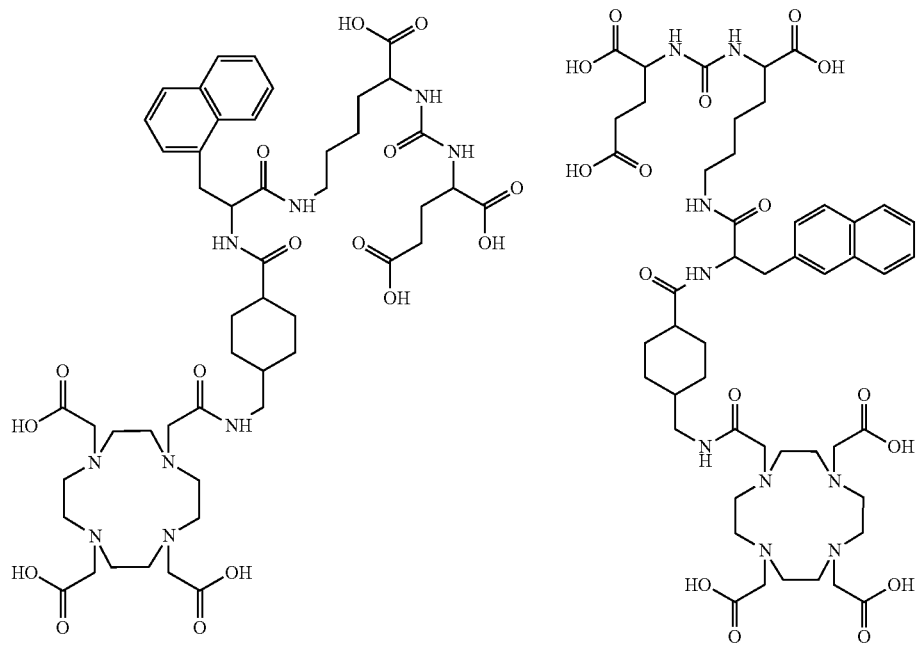
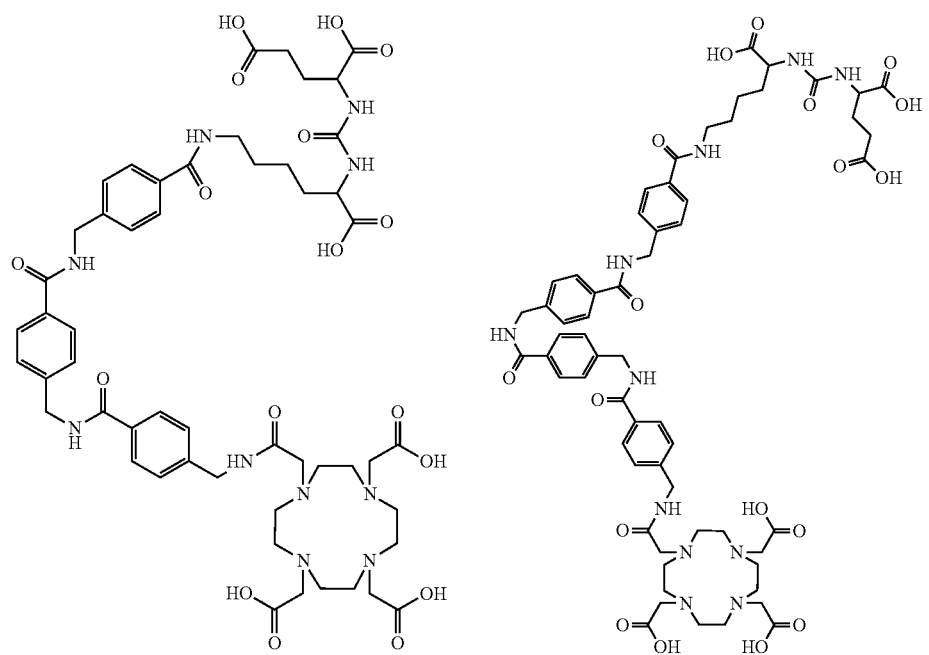

-continued
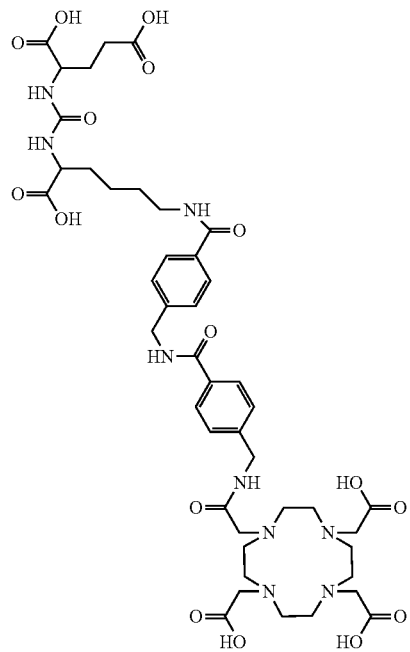
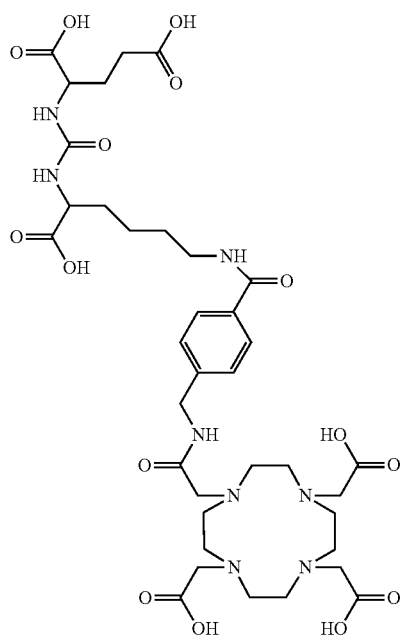
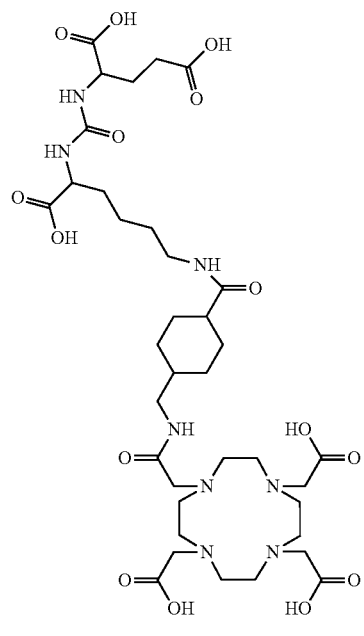
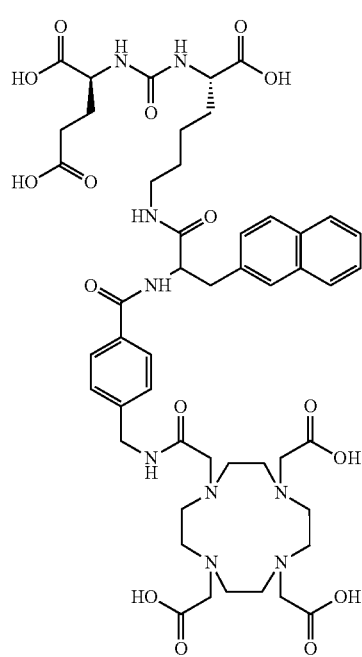
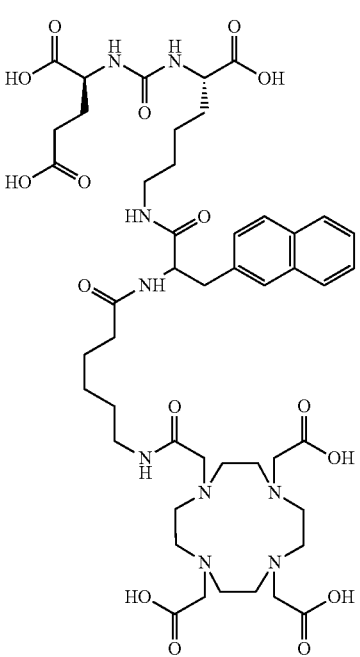

-continued
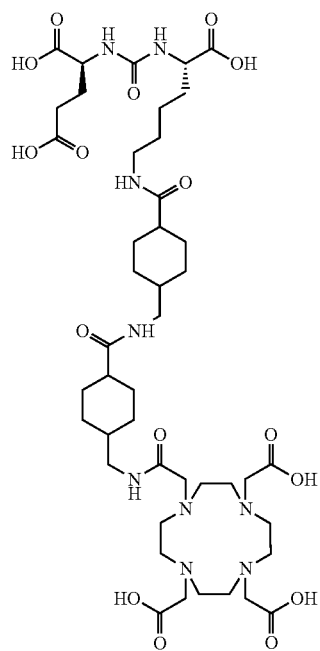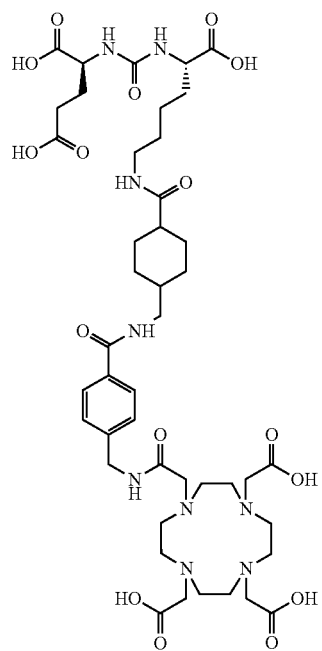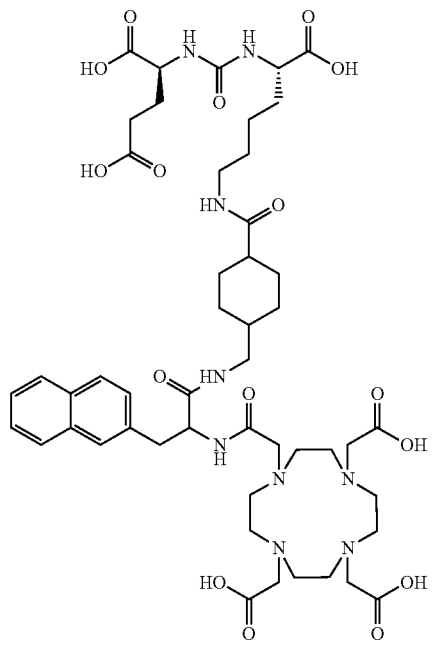
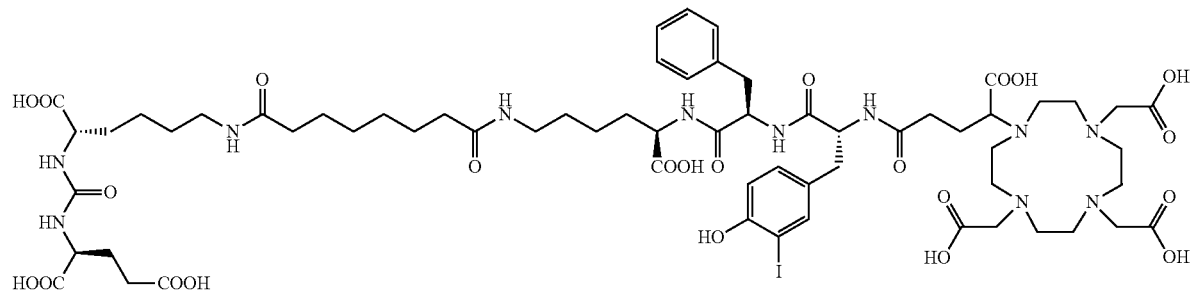
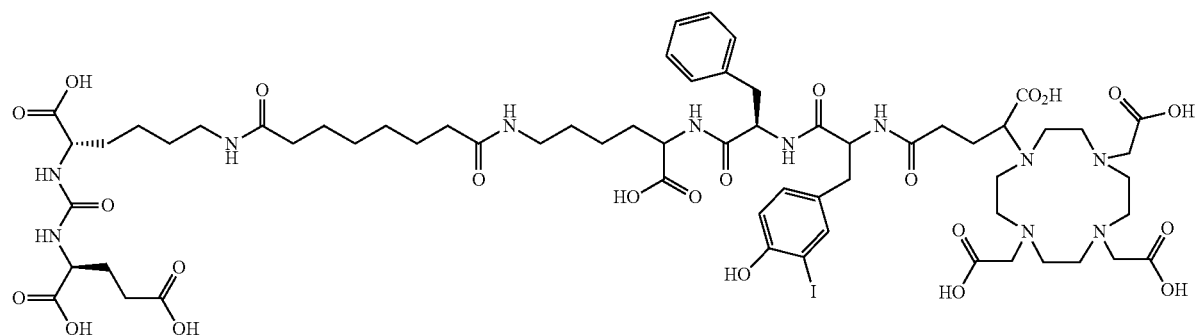

Among the particularly preferred compounds useable in the present invention is the Ac-225-radiopharmaceutical called Ac-225-PSMA-617. Ac-225-PSMA-617 is a compound according to the following formula

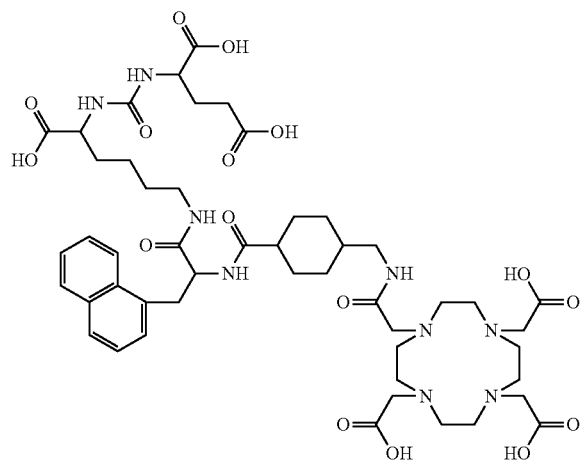 [SMILES: O=C(O)CCC(NC(=O)NC(CCCCNC(=O)C(Cc1cccc2ccccc12)NC(=O)C1CCC(CNC(=O)CN2CCN(CC(=O)O)CCN(CC(=O)O)CCN(CC(=O)O)CC2)CC1)C(=O)O)C(=O)O]

chelating a Ac-225 radionuclide with its 1,4,7,10-tetraazacyclododecane-N,N',N'',N'''-tetraacetic acid moiety.

The effective amount of said one or more of Ac-225-radiopharmaceuticals is administered as a dosage of from about 25 kBq/kg to about 400 kBq/kg of body weight of said patient or wherein the effective amount of said Ac-225-radiopharmaceutical is administered as a unitary dosage or constant activities of from about 3 MBq to about 30 MBq to said patient.

It has been surprisingly found that radiopharmaceuticals comprising Ac-225 as a radionuclide provide considerably and significantly better therapeutic results as corresponding radiopharmaceuticals with other radionuclides, especially with the particular administration dosages of the present invention as will become apparent from the description below.

In a second aspect, the present invention concerns the use of one or more Ac-225-radiopharmaceuticals as mentioned above for treating PSMA expressing cancers or cancer cells in a patient, wherein the use comprises administering to said patient an effective amount of said Ac-225-radiopharmaceutical as a dosage of from about 25 kBq/kg to about 400 kBq/kg of body weight of said patient or as a unitary dosage or constant activities of from about 3 MBq to about 30 MBq to said patient.

In a third aspect, the invention relates to one or more Ac-225-radiopharmaceuticals selected among those mentioned above for use in treating PSMA expressing cancers or cancer cells in a patient, comprising administering to said patient an effective amount of said Ac-225-radiopharmaceutical(s) as a dosage of from about 25 kBq/kg to about 400 kBq/kg of body weight of said patient or as a unitary dosage or constant activities of from about 3 MBq to about 30 MBq to said patient.

It has been surprisingly found that treating patients having PSMA expressing cancers or cancer cells with Ac-225-radiopharmaceuticals, i.e. radiopharmaceuticals comprising Ac-225 as a radionuclide, as described herein allows for a particularly strong anticancer effect with low hematotoxicity as will be shown in greater detail below.

The PSMA expressing cancers may be any cancer whose cancerous cells express Prostate Specific Membrane Antigen (PSMA). Preferably cancers (or cancer cells) that may be treated according to the invention are selected among prostate cancer, conventional renal cell cancers, cancers of the transitional cells of the bladder, testicular-embryonal cancers, neuroendocrine cancers, colon cancers, brain tumors and breast cancers. In particularly preferred aspects of the invention, said PSMA expressing cancer is prostate cancer or breast cancer.

The cells of said PSMA expressing cancers or cancer cells may be treated not only within a solid tumor, but also after dissemination. Hence, in a particularly preferred aspect, the invention relates to the treatment of a disseminated cancer or cancer cells. Indeed, the very efficient and specific targeting of the Ac-225-radiopharmaceuticals to PSMA combined to the short range (<100 micrometers) action of the Ac-225 alpha emitter allows for very good results of destruction of cancer cells without notable damage to non-target tissues, as further described below.

The effective amount of said one or more Ac-225-radiopharmaceuticals to be administered to a patient generally is determined in light of the patient's case. However, the effective amount thereof will represent a dosage within a range from about 25 kBq/kg to about 400 kBq/kg of body weight of said patient. More particularly, the dosage may preferably range from about 30 kBq/kg to about 250 kBq/kg of body weight, for example about 30, 40, 50, 60, 70, 80, 90, 100, 110, 120, 130, 140, 150, 160, 170, 180, 190, 200, 210, 220, 230, 240 or 250 kBq/kg, or any range between any two of the above values.

Alternatively, the effective amount may be administered as a unitary dosage or constant activities, such as from about 3 MBq to about 30 MBq for one administration to the patient. Preferably the unitary dosage or constant activities range from about 4 MBq to about 25 MBq per administration, in particular about 5 MBq to about 20 MBq, such as for example about 5, 6, 7, 8, 9, 10, 11, 12, 13, 14, 15, 16, 17, 18, 19 or 20 MBq, or any range between any two of the above values.

If necessary or desirable, the treatment may comprise more than one administration of an effective amount of one or more Ac-225-radiopharmaceuticals as described above. Indeed it is generally beneficial to repeat, one or more times, the administration of an effective amount of said one or more Ac-225-radiopharmaceuticals to the patient after 15 to 90 days, such as at a one- or two-month intervals. Neither the effective amount of such repeated administration, nor the intervals between multiple consecutive administrations need to be the same as those of previous administrations or repetitions.

Bq, kBq and MBq represent the SI unit becquerel, as well as its multiples kilobecquerel ($10^3$ Bq) and megabecquerel ($10^6$ Bq) respectively, wherein 1 Bq corresponds to the activity of a quantity of radioactive material in which one nucleus decays per second.

An "effective amount" in the context of the invention is an amount of Ac-225-radiopharmaceutical(s) that produces at least some measurable therapeutic response or desired effect in some fraction of the patient to whom it is administered. The effective amount may be expressed as dosage per weight unit of the patient (and per administration), such as kBq/kg body weight of the patient or as a unitary dosage (also called "constant activity"), meaning a dosage for one administration to one patient independently of the patient's weight, such as MBq.

The terms "administer", "administering" and "administration" refer to the giving of the Ac-225-radiopharmaceutical(s) to a patient by any appropriate route. In particular, the Ac-225-radiopharmaceutical(s) may be administered by oral or parenteral route, preferably parenteral route, such as by injection or infusion, wherein the injection or infusion may be made intravenously, intramuscularly, intra-arterially, subcutaneously, intra-dermally, intraperitoneally, etc. Depending on the administration route, the Ac-225-radiopharmaceutical(s) may comprise further appropriate constituents, such as carriers, solvents and excipients generally known in the art.

All approximate values given herein as indicated by the presence of the word "about" include a range of +/−10% centered on said value.

BRIEF DESCRIPTION OF THE DRAWINGS

Preferred embodiments of the invention will now be described, by way of example, with reference to the accompanying drawings in which.

Figure 1:
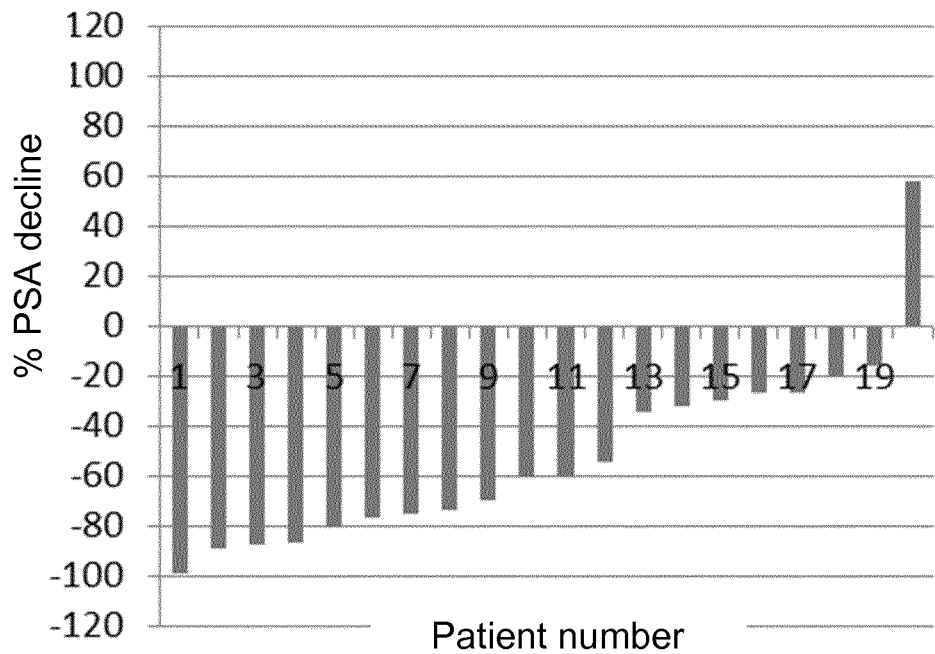
FIG. 1 is a graph of experimental data showing the decrease in PSA (Prostate-Specific Antigen) (%) after first treatment with Ac-225-PSMA-617.

Further details and advantages of the present invention will be apparent from the following detailed description of the not limiting embodiments with reference to the attached drawings below.

DESCRIPTION OF PREFERRED EMBODIMENTS

A1. Peptide, Radionuclides and Radiolabeling

PSMA-617 was obtained from ABX, Germany.

Ac-225 (also noted $^{225}$Ac) was produced by radiochemical extraction from Th-229 as described in Apostolidis C, Molinet R, Rasmussen G, Morgenstern A., Production of Ac-225 from Th-229 for targeted alpha therapy. Analytical Chemistry, 2005; 77(19):6288-91 and Zielinska B, Apostolidis C, Bruchertseifer F, Morgenstern A., An Improved Method for the Production of Ac-225/Bi-213 from Th-229 for Targeted Alpha Therapy, Solvent Extraction and Ion Exchange, 2007; 25(3):339-49.

For radiolabeling an aliquot of Ac-225 stock solution (6-39 MBq Ac-225) in 0.1 M hydrochloric acid was added into a microwave vial containing 0.5 ml of 0.1 M Tris buffer (pH 9) and an appropriate amount of 10 mM PSMA-617 stock solution (35-160 nMol peptide). The reaction mixture was heated to 95° C. for 5 min using a microwave synthesizer (Biotage® Initiator) and subsequently cooled to <50° C. using pressurized air.

Quality control was performed by instant thin layer chromatography (ITLC-SG, Pall Life Sciences) with 0.05 M citric acid (pH 5) as solvent. Under these conditions, unbound Ac-225 moves with the solvent front (Rf=1), while Ac-225-PSMA-617 remains on the bottom of the strip (Rf=0). After development the ITLC strip was stored for at least 1 hour until radiochemical equilibrium between Ac-225 and its daughter nuclide Fr-221 ($T_{1/2}$=4.8 min) was obtained. Subsequently radiochemical purity was determined by measuring the activity of the 218 keV gamma emission of Fr-221 on the upper and lower part of the ITLC strip using high resolution gamma spectrometry (Ortec).

After synthesis 0.5 ml of 18% ascorbic acid solution (pH 5.8) was added to the reaction mixture to minimize radiolytic degradation of Ac-225-PSMA-617. The final pH of the formulation was 7.4. Before injection, sterility of the final formulation was assured via sterile filtration (Millex-GV, 0.20 μm, Millipore).

Gallium-68-PSMA11 PET/CT imaging was performed using a radiotracer labeled with Ga-68.

A2. Results

Radiochemical purity was 98.6±1.4% (n=67), specific activity was 0.23±0.1 MBq per nmol of peptide.

A3. Patient Treatment

20 Patients were treated 3 times with activities of 100 kBq/kg body weight of Ac-225-PSMA-617 in two month intervals.

Treatment response was monitored by PSA values in blood and with PET/CT (positron emission tomography-computed tomography) with Ga-68-PSMA-HBED-CC (also called Gallium-68-PSMA11) before therapy and after the third therapy.

Toxicity was monitored by blood sampling.

A4. Results

A4.1 Treatment Efficacy

Eight weeks after the first treatment cycle 19/20 patients presented a decrease in PSA, in 17 patients the decrease was >25%, in 12 patients the decrease was even >50%.

The graph of FIG. 1 shows the decrease in PSA (%) after a first treatment with Ac-225-PSMA-617.

Sixteen weeks after the first treatment cycle 15/20 patients presented a decrease in PSA, in 14 patients the decrease was >50%.

Figure 2:
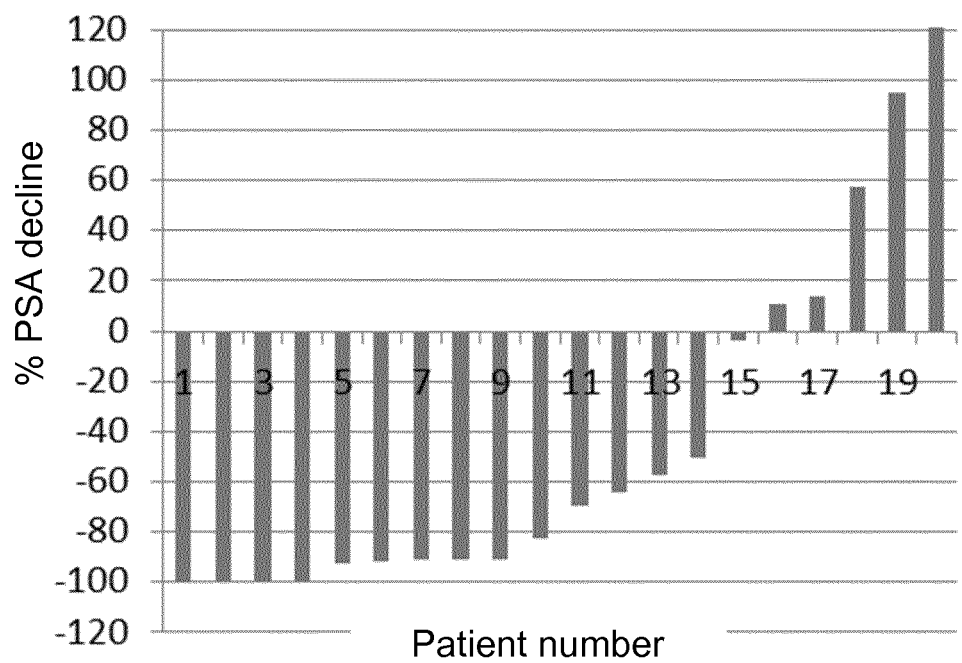
FIG. 2 is a graph of experimental data illustrating the decrease in PSA (%) after a second treatment with Ac-225-PSMA-617.

As illustrated by the graph of FIG. 2 the decrease in PSA (%) after a second treatment with Ac-225-PSMA-617.

Twenty-four weeks after the first treatment cycle 15/20 patients presented with a decrease in PSA, in 12 patients the decrease was even >50%.

Figure 3:
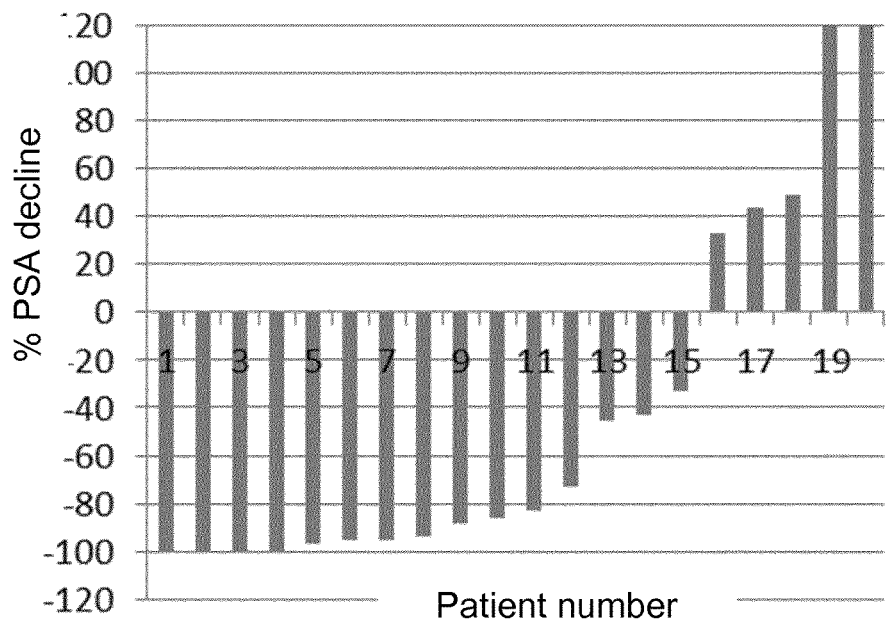
FIG. 3 is a graph of experimental data representing the decrease in PSA (%) after third treatment with Ac-225-PSMA-617.

FIG. 3 shows the decrease in PSA (%) after third treatment with Ac-225-PSMA-617.

Figure 4:
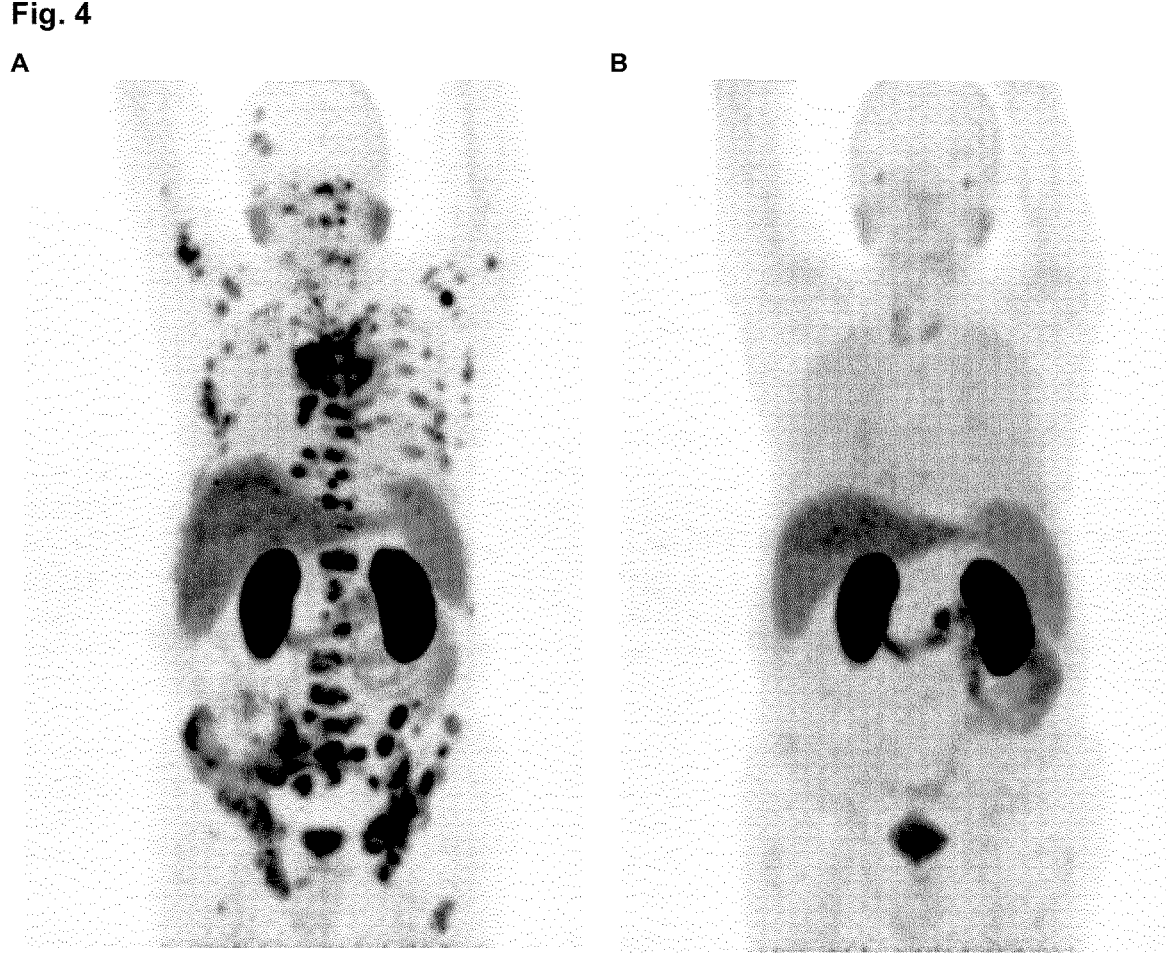
FIGS. 4 to 6 show Gallium-68-PSMA11 PET/CT imaging of three patients before (FIGS. 4A, 5A and 6A) and after (FIGS. 4B, 5B and 6B) therapy as described herein below.
Figure 5:
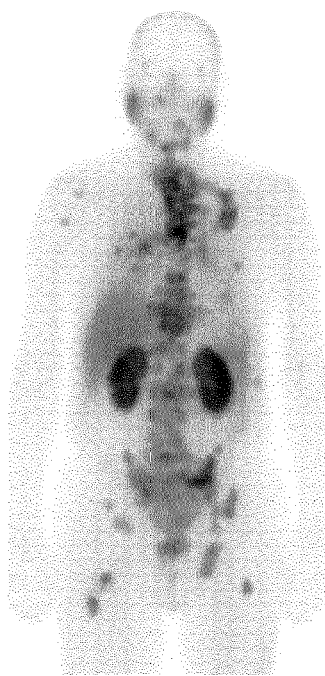
Figure 5:
Figure 6:
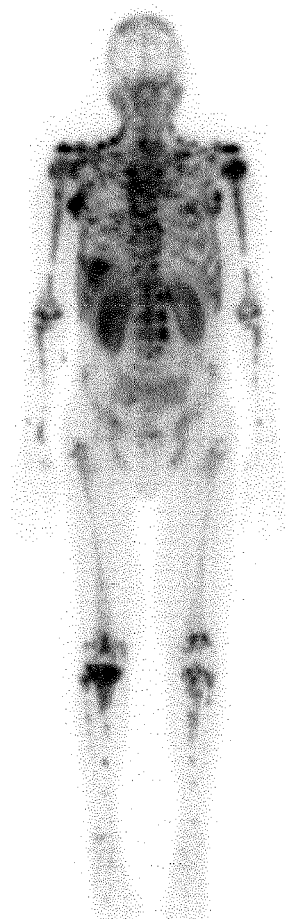
Figure 6:

The exceptional results obtainable by the present invention are illustrated in FIGS. 4 to 6. These figures show PET/CT images of three different patients before and after the treatment as described above. The PET/CT imaging combines both a positron emission tomography (PET) scanner and an x-ray computed tomography (CT) scanner, so that images acquired from both devices can be taken sequentially, in the same session, and combined into a single superposed image. As can be seen the betterment of the patients' condition is most remarkable.

A4.2 Toxicity

Figure 7:
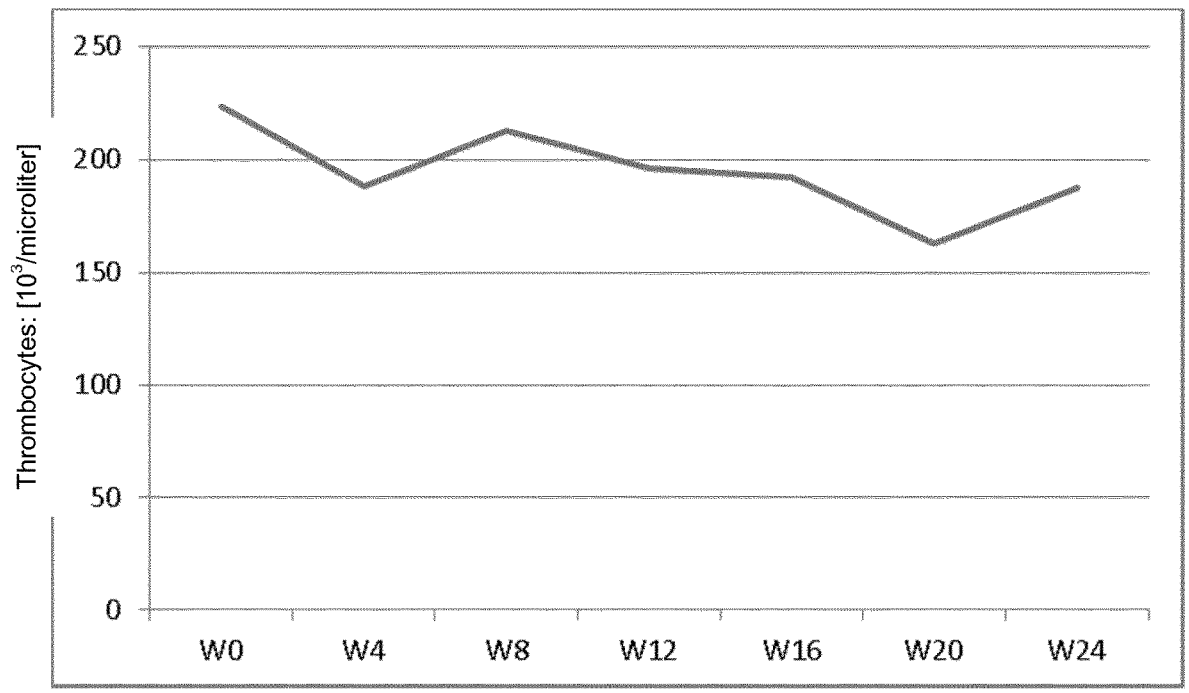
FIG. 7 illustrates the development of thrombocyte count during Ac-225-PSMA-617 therapy as described herein below.
Figure 8:
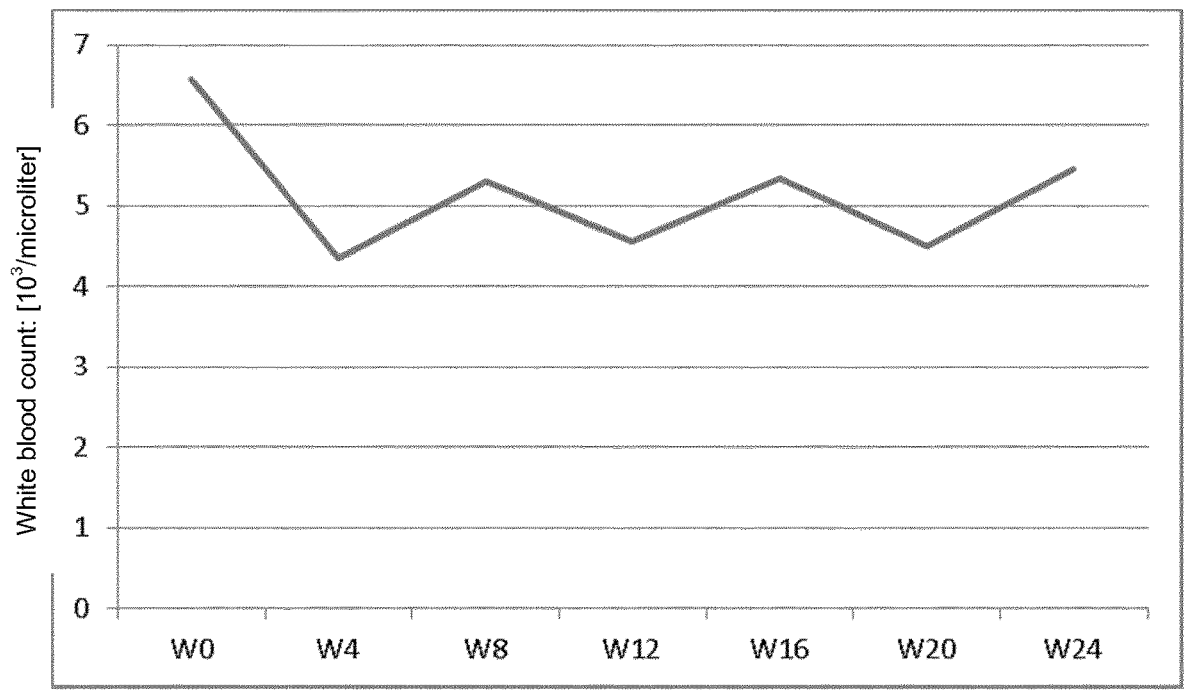
FIG. 8 shows the development of leukocyte count during Ac-225-PSMA-617 therapy as described herein below.

Hematologic response was evaluated every 4 weeks per lab tests and clinical side effects were monitored every 8 weeks. The treatment was well tolerated. There was no significant change in thrombocyte or white blood cell count (FIGS. 7 and 8). Several patients reported dysfunction of salivary glands.

FIG. 7 shows the development of thrombocyte count during Ac-225-PSMA-617 therapy, whereas FIG. 8 displays the development of leukocyte count during Ac-225-PSMA-617 therapy.

A5. Conclusions of the Above Experiments

The inventors found that treatment response with said Ac-225-radiopharmaceutical(s) is very good and hematologic toxicity is moderate to low at dosages of about 100 kBq/kg body weight (i.e. about 7 MBq for a patient of 70 kg). The treatment may be done using a unitary dosage or constant activities, e.g. about 6 MBq per treatment. Furthermore, the patients may be treated in eight week or two month intervals for practical reasons. Shorter intervals (e.g. four weeks or one month) with correspondingly lower dosing are also possible.

A6. Comparative Examples

Experiments have been conducted to compare the efficiency of the Ac-225-radiopharmaceuticals as used in the present invention, such as Ac-225-PSMA-617, with that of non-Ac-225-radiopharmaceuticals comprising the same targeting compound, but chelated e.g. with Lu-177, such as a radionuclide Lu-177-PSMA-617.

A6.1 Treatment Efficacy

Eight weeks after the first treatment cycle 21/30 patients presented a decrease in PSA, In 16 patients the decrease was >50%.

Twenty-four weeks after the first treatment cycle some patients were dropped out from the therapy because some physical conditions were considered a contraindication for treatment with β-emitters. 9/30 patients presented a decreased in PSA. For all of them the decrease was >50%.

Figure 9:
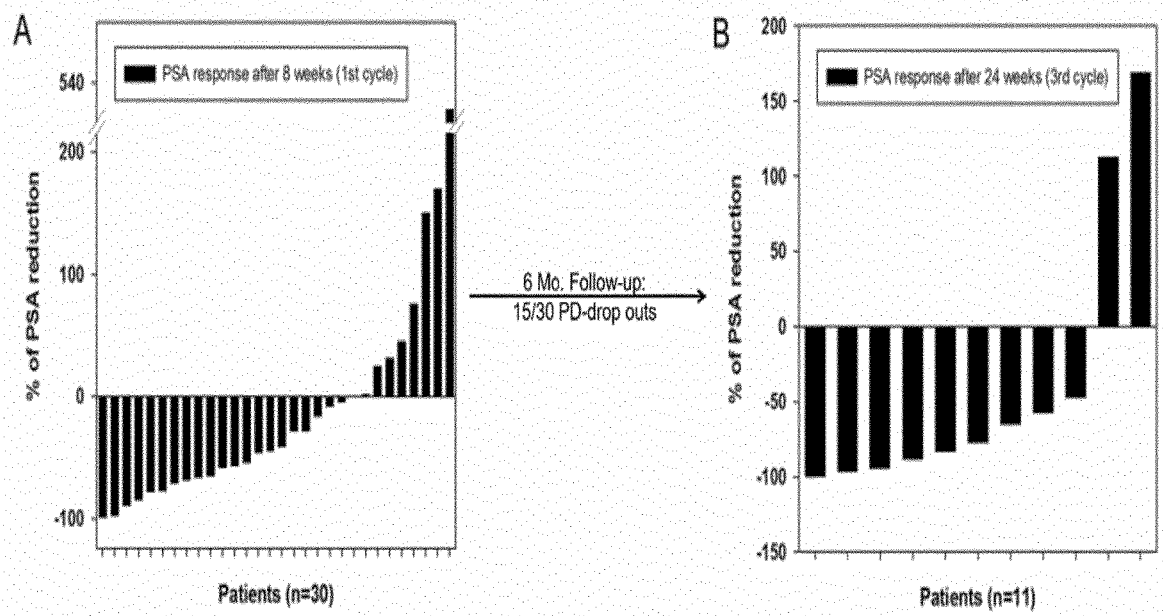
FIG. 9 is a graph of experimental data showing the decrease in PSA (%) after first treatment and after third treatment with Lu-177-PSMA-617.

The graph of FIG. 9 shows the decrease in PSA (%) after a first and a third treatment with Lu-177-PSMA-617.

A6.2 Toxicity

Figure 10:
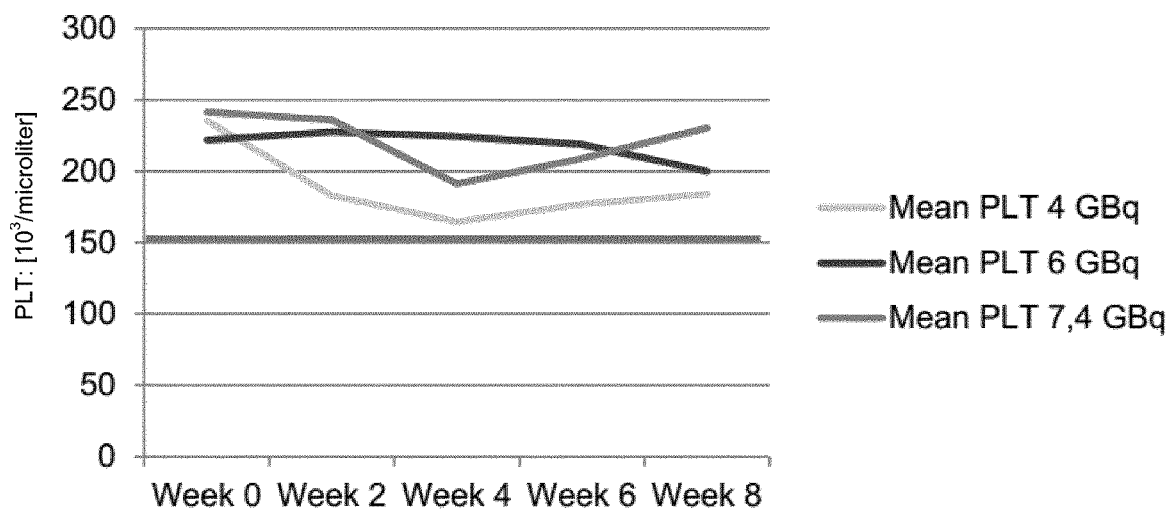
FIG. 10 shows the development of thrombocyte count during Lu-177-PSMA-617 comparative experiments as described herein below.
Figure 11:
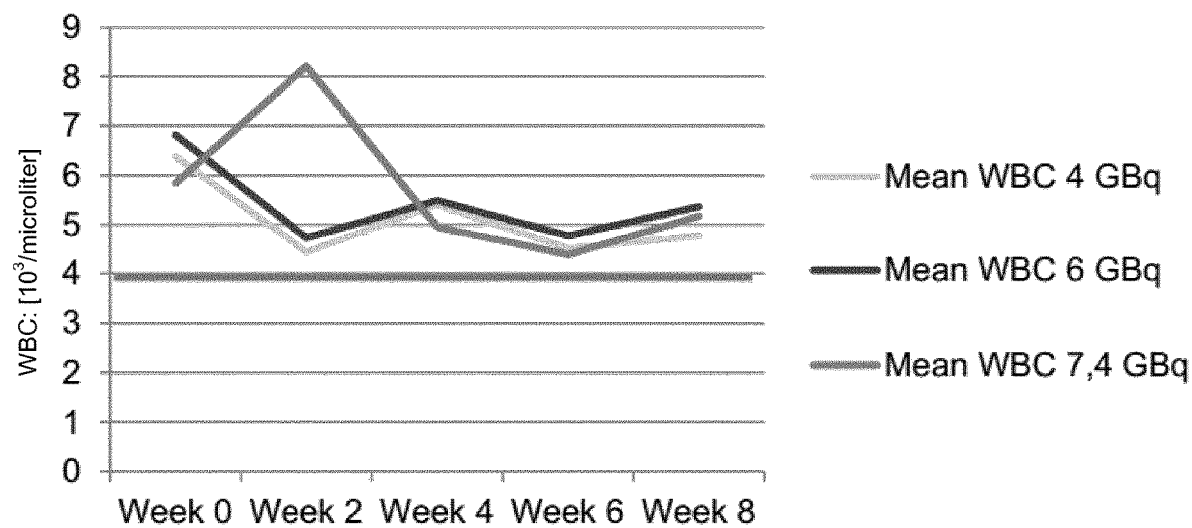
FIG. 11 illustrates the development of leukocyte count during Lu-177-PSMA-617 comparative experiments as described herein below.

The treatment was well tolerated. There was no significant change in thrombocyte or white blood cells count (FIGS. 10 and 11). Mild moderate dysfunction of salivary glands was reported.

FIG. 10 shows the development of thrombocyte count during Lu-117-PSMA-617 therapy, whereas FIG. 11 displays the development of leukocyte count during Lu-117-PSMA-617 therapy.

A6.3 Conclusions of the Above Comparative Experiments

The group treated with Lu-117-PSMA-617 had a lower response rate in comparison to the one treated with Ac-225-PSMA-617. Indeed, the treatment analysis revealed that 15/28 patients (54%) treated with Ac-225-PSMA-617 were in PSA response but only 9/30 patients (30%) treated with Lu-177-PSMA-617 were in PSA response at week-24. This is a remarkable difference taking into account similar hematological toxicity and the more advanced patients selected for Ac-225-radiopharmaceutical therapy.

Figure 12:
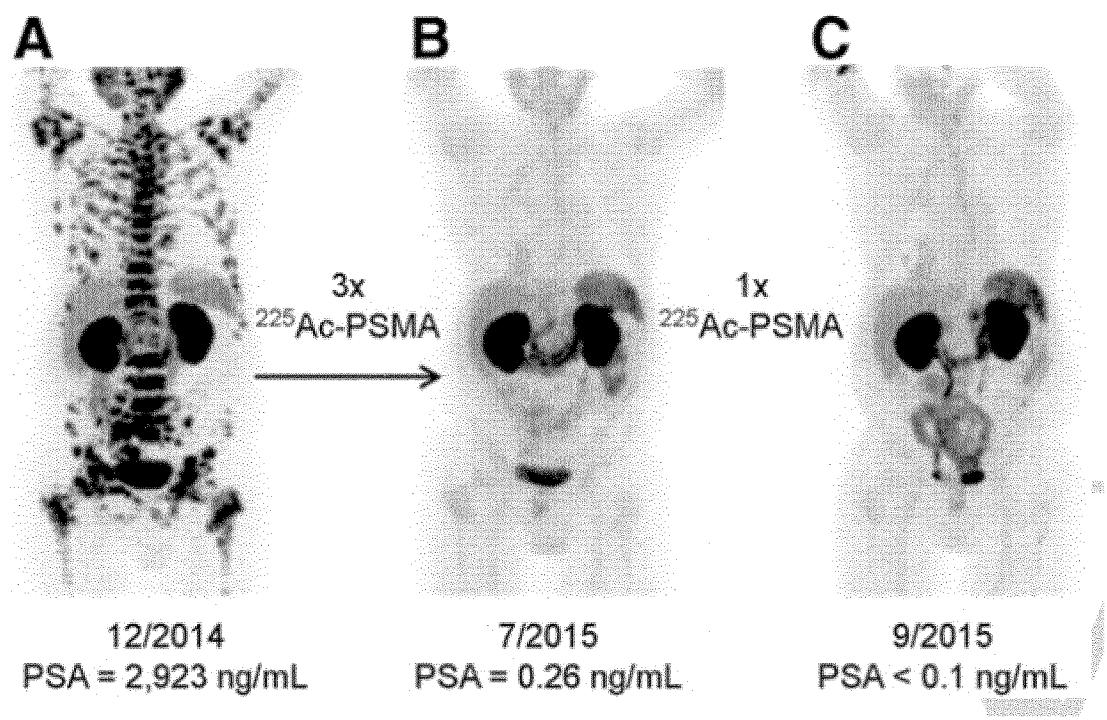
FIG. 12 shows Ga-68-PSMA-11 PET/CT scans of a patient: pretherapeutic tumor spread (A), restaging 2 months after third cycle of Ac-225-PSMA-617(B), and restaging 2 months after one additional consolidation therapy (C)

B1. Treatment of Metastatic Castration-Resistant Prostate Cancer (mCRPC) with Ac-225-Rad Iopharm Aceutical FIG. 12: Ga-68-PSMA-11 PET/CT scans of patient A. Pretherapeutic tumor spread (A), restaging 2 months after third cycle of Ac-225-PSMA-617(B), and restaging 2 months after one additional consolidation therapy (C).

Clinical Course of Patient A presented with diffuse red marrow infiltration of mCRPC (this physical condition was considered a contraindication for treatment with β-emitters). Patient A was treated with 3 cycles of 9-10 MBq (100 kBq per kilogram of body weight) of Ac-225-PSMA-617 at bimonthly intervals. Posttherapeutic emission scans validated sufficient tumor targeting Two months later, all previously PSMA-positive lesions had visually disappeared on PSMA PET/CT (FIG. 12B) and, accordingly, the PSA level had dropped from more than 3,000 ng/ml to 0.26 ng/ml. The patient received an additional 6 MBq of Ac-225-PSMA-617 as consolidation therapy, resulting in a further PSA decline to less than 0.1 ng/ml along with a complete imaging response (FIG. 1C).

Figure 13:
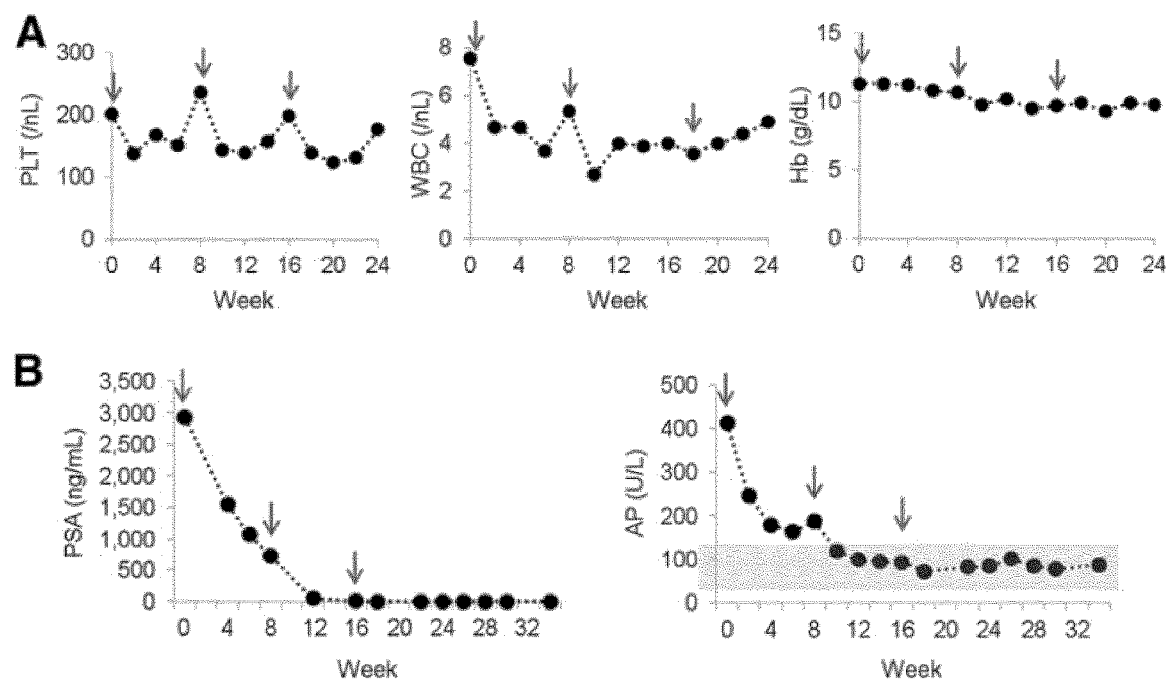
FIG. 13 illustrates laboratory test follow-up of a patient; arrows indicate administration of treatment cycles; (A) blood cell count demonstrates moderate hematologic toxicity; (B) decline of tumor markers to none measurable or reference range correlates with imaging response.

FIG. 13: Laboratory test follow-up of patient A. Arrows indicate administration of treatment cycles. (A) Blood cell count demonstrates moderate hematologic toxicity. (B) Decline of tumor markers to none measurable or reference range correlates with imaging response. AP=alkalinephosphatase; Hb=5 hemoglobin; PLT=platelets; WBC=white blood cells.

After each cycle, the blood cell count and alkaline phosphatase level were checked every 2 week. The platelet level never dropped below 100/nl (grade 1 according to the Common Terminology Criteria for Adverse Events, version 4.0), the total white blood cell count never dropped below 2.5/nl (grade 1), and the hemoglobin level never dropped below 9.5 g/dl (grade 2) (FIG. 13A). Moderate but enduring dysfunction of salivary glands was the only clinically reported side effect. A concordant decline in PSA level and alkaline phosphatase level (FIG. 13B) further underlined the excellent treatment response.

B2 Treatment with Lu-177 then Ac-225

Figure 14:
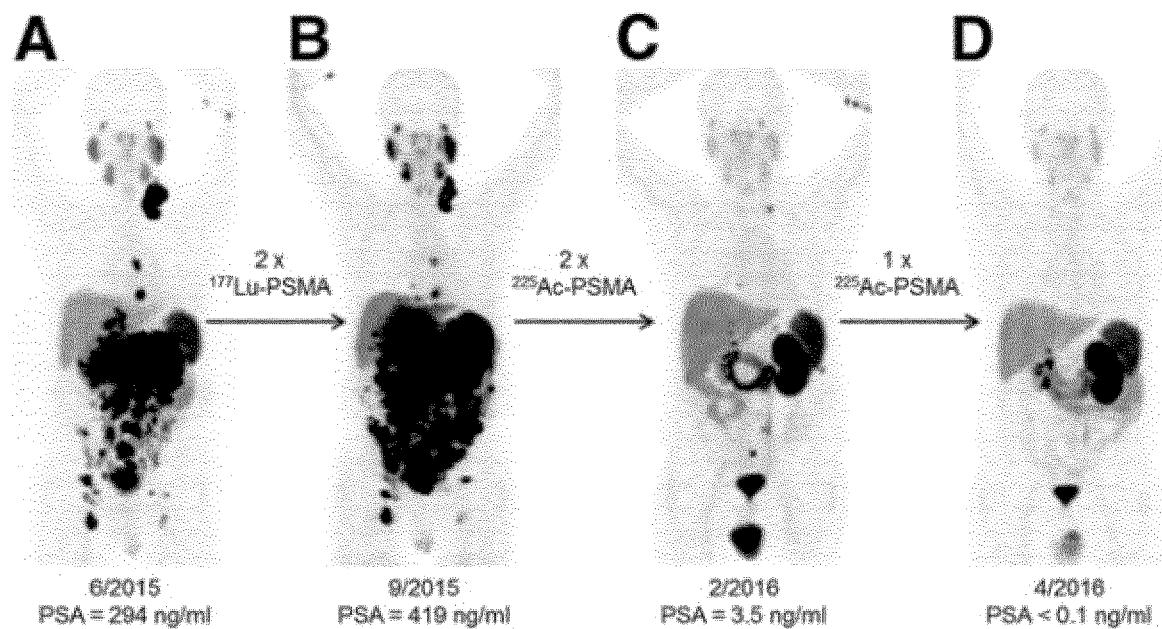
FIG. 14 show 68-Ga-PSMA-11 PET/CT scans of another patient; in comparison to initial tumor spread (A), restaging after 2 cycles of β-emitting Lu-177-PSMA-617 presented progression (B); in contrast, restaging after second (C) and third (D) cycles of α-emitting Ac-225-PSMA-617 presented impressive response.

FIG. 14: 68-Ga-PSMA-11 PET/CT scans of patient B. In comparison to initial tumor spread (A), restaging after 2 cycles of β-emitting Lu-177-PSMA-617 presented progression (B). In contrast, restaging after second (C) and third (D) cycles of α-emitting Ac-225-PSMA-617 presented impressive response.

Clinical Course of Patient B presented with peritoneal carcinomatosis and liver metastases.

Figure 15:
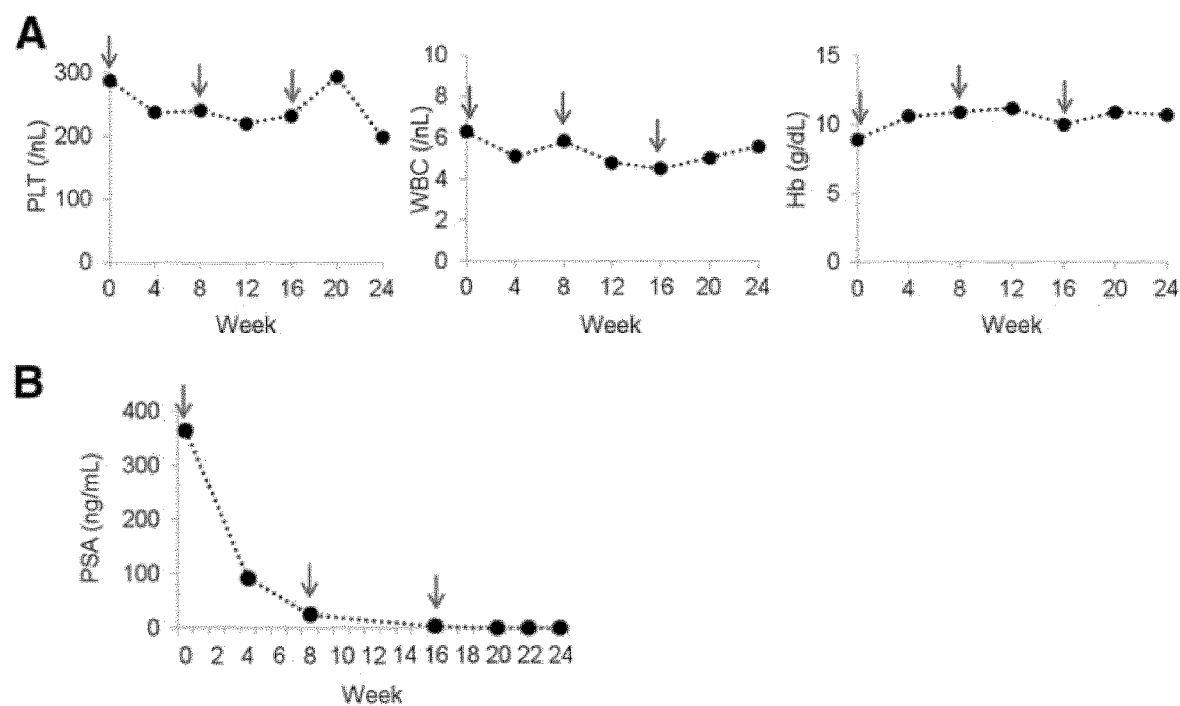
FIG. 15 illustrates laboratory test follow-up of a patient; arrows indicate administration of treatment cycles; blood cell count (A) always stayed in reference range, and tumor marker PSA (B) finally declined to none measurable.

Patient B was initially treated with Lu-177-PSMA-617 (7.4 GBq per cycle), which was offered as salvage therapy. The initial PSA level was 294 ng/ml. After cycle 2 the PSA level increased to 419 ng/ml and most lesions demonstrated tumor progression on PSMA PET/CT (FIG. 14B). Therapy was changed to Ac-225-PSMA-617, and the patient received 3 cycles of 6.4 MBq (100 kBq per kilogram of body weight) at bimonthly intervals. Restaging based on the PSMA PET/CT results finally indicated a partial response after 2 cycles (FIG. 14C) and a complete remission after 3 cycles (FIG. 14D). Laboratory tests revealed no relevant hematologic toxicity; PSA dropped to below the measurable level (0.1 ng/ml) (FIG. 15). However, the patient reported severe dysfunction of salivary glands.

FIG. 15: Laboratory test follow-up of patient B. Arrows indicate administration of treatment cycles. Blood cell count (A) always stayed in reference range, and tumor marker PSA (B) finally declined to none measurable.

B3. Conclusion

The early results already indicate that Ac-225-targeted α-therapy has high potential for the epidemiologically important tumor entity prostate cancer, which presumably will further accelerate the routine availability of Ac-225 for systematic clinical trials, for example.

The two impressive responses reported here demonstrate the high potential of Ac-225-radiopharmaceuticals, such as Ac-225-PSMA-617 to significantly benefit mCRPC patients who are in a clinically critical situation, that is, patients with diffuse red marrow infiltration and resistance to other therapies. Investigation of this therapeutic modality in larger patient cohorts is warranted.

The invention claimed is:

1. A method for treating PSMA expressing cancers, wherein the method comprises administering to a patient in need thereof an effective amount of one or more Ac-225-radiopharmaceuticals, said one or more Ac-225-radiopharmaceuticals comprising Ac-225 chelated with a targeting compound of Formula (A), (B), (C), (D) or (E):

Formula (A)

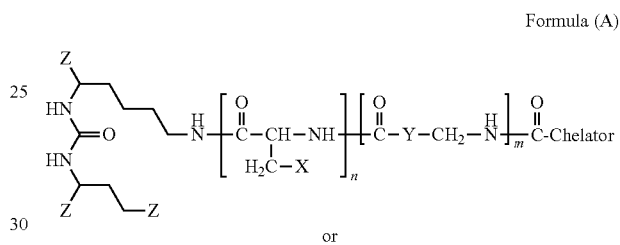

or

Formula (B)

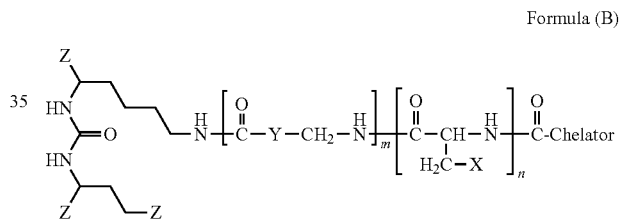

with:
n: 0, 1
m: 1, 2, 3, 4
Z: —CO₂H, —SO₂H, —SO₃H, —SO₄H, —PO₂H, —POSH, —PO₄H₂
X: naphthyl, phenyl, biphenyl, indolyl (=2,3-benzopyrrolyl), benzothiazolyl
Y: aryl, alkylaryl, cyclopentyl, cyclohexyl, cycloheptyl
Chelator: 1,4,7,10-tetraazacyclododecane-N,N',N'',N'''-tetraacetic acid (DOTA),
    N,N''-bis[2-hydroxy-5-(carboxyethyl)benzyl]ethylenediamine-N,N''-diacetic acid (HBED-CC),
    1,4,7-triazacyclononane-1,4,7-triacetic acid (=NOTA),
    2-(4,7-bis(carboxymethyl)-1,4,7-triazonan-1-yl) pentanedioic acid (NODAGA),
    2-(4,7,10-tris(carboxymethyl)-1,4,7,10-tetraazacyclododecan-1-yl)pentanedioic acid (DOTAGA),
    1,4,7-triazacyclononane phosphinic acid (TRAP),
    1,4,7-triazacyclononane-1-[methyl(2-carboxyethyl) phosphinic acid]-4,7-bis[methyl(2-hydroxymethyl)phosphinic acid] (NOPO),
    3,6,9,15-tetraazabicyclo[9.3.1]pentadeca-1(15), 11,13-triene-3,6,9-triacetic acid (PCTA), N'-{5-[Acetyl(hydroxy)amino]pentyl}-N-[5-({4-[(5-aminopentyl)-(hydroxy)amino]-4-oxobutanoyl}amino)pentyl]-N-hydroxysuccinamide (DFO),
diethylenetriaminepentaacetic acid (DTPA),
Trans-cyclohexyl-diethylenetriaminepentaacetic acid (CHX-DTPA),
1-oxa-4,7,10-triazacyclododecane-4,7,10-triacetic acid (oxo-Do3A) p-isothiocyanatobenzyl-DTPA (SCN-Bz-DTPA),
1-(p-isothiocyanatobenzyl)-3-methyl-DTPA (1B3M),
2-(p-isothiocyanatobenzyl)-4-methyl-DTPA (1M3B), or
1-(2)-methyl-4-isocyanatobenzyl-DTPA (MX-DTPA)

or

Formula (C)

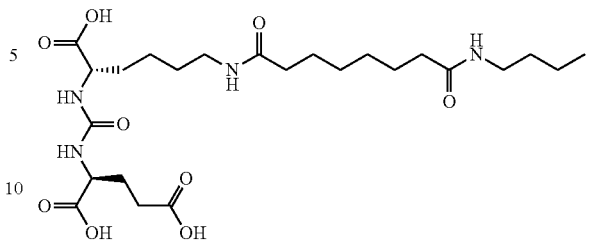

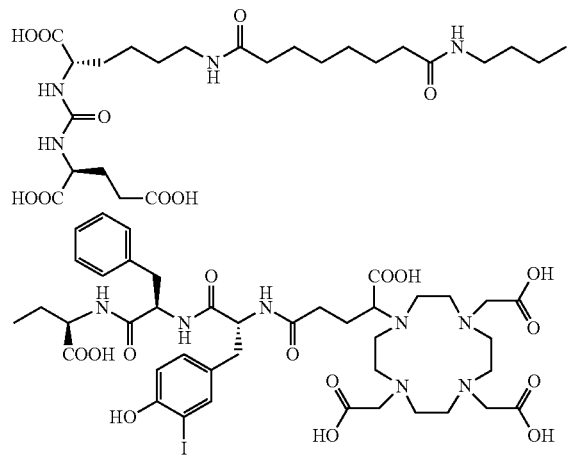

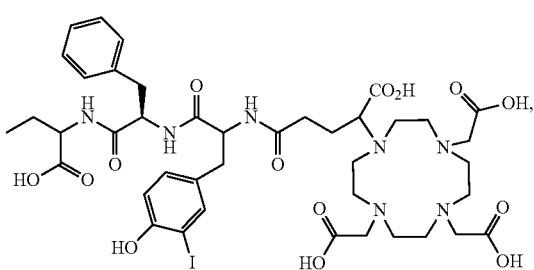

Formula (D)

Formula (E)

(PSMA antibody)-Chelator or (PSMA minibody)-Chelator;

wherein the effective amount of said one or more Ac-225-radiopharmaceuticals is administered as a dosage of from 25 kBq to 400 kBq/kg of body weight of said patient or wherein the effective amount of said one or more Ac-225-radiopharmaceuticals is administered as a unitary dosage of from 3 MBq to 30 MBq to said patient.

2. The method of claim 1, wherein the one or more Ac-225-radiopharmaceuticals are selected from:

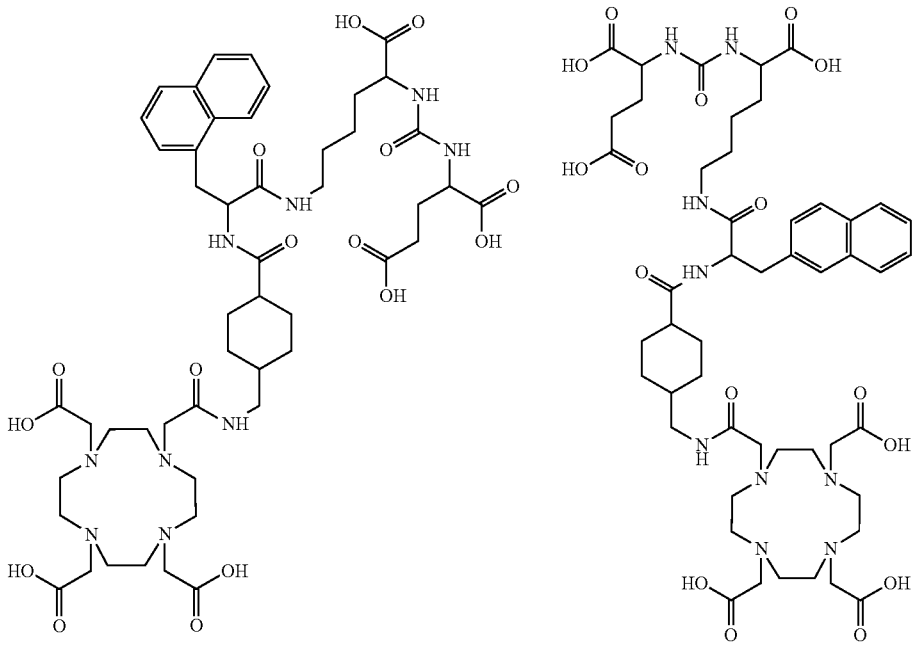

-continued
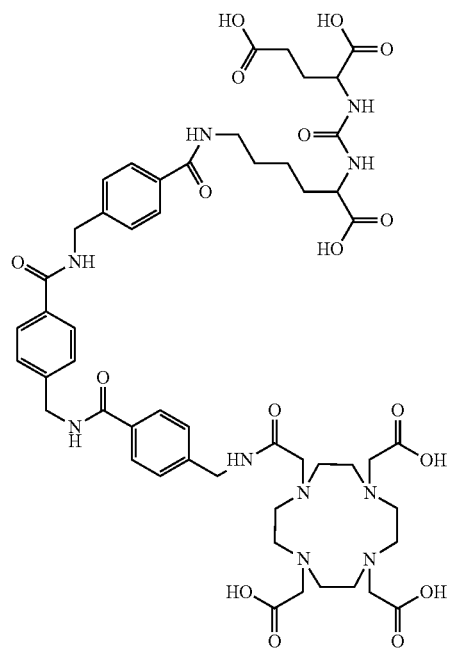
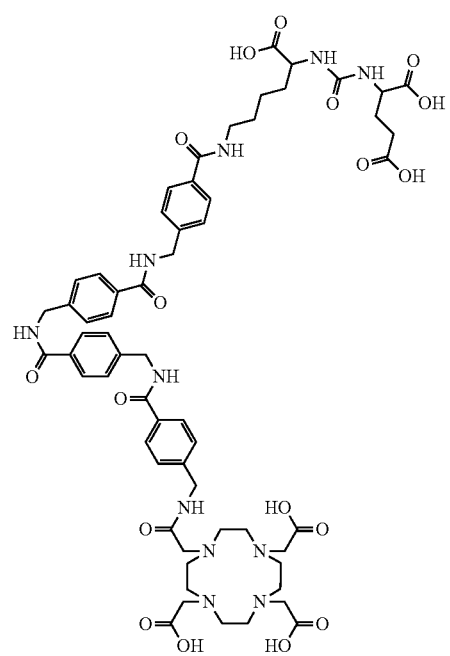
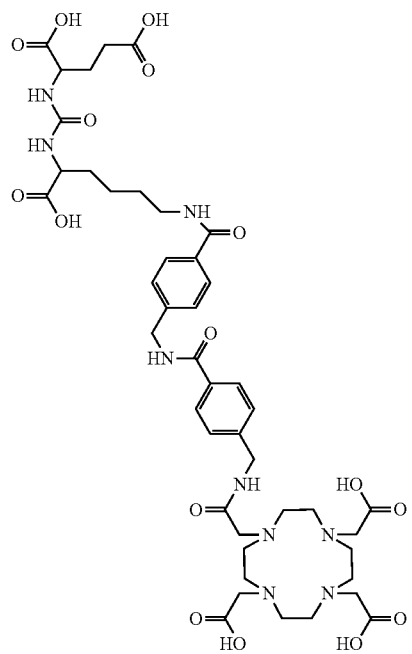
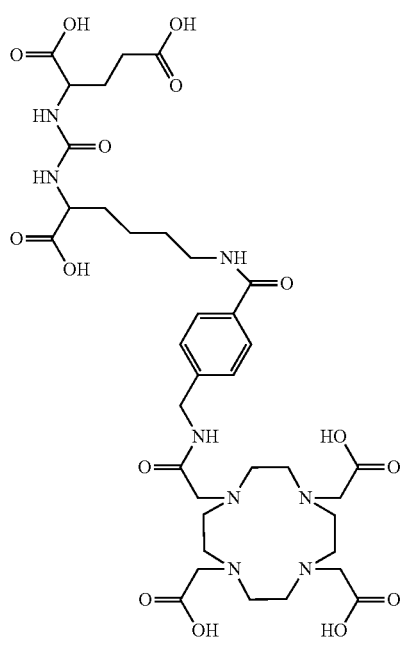

23
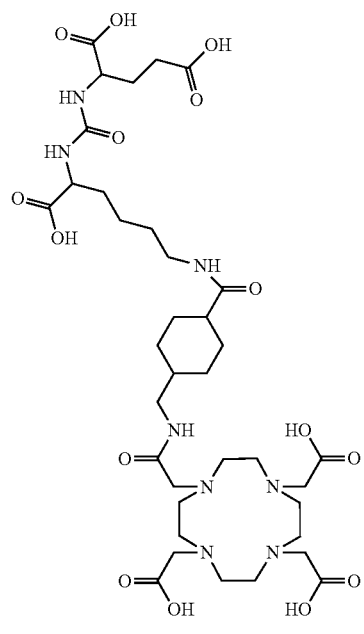
24
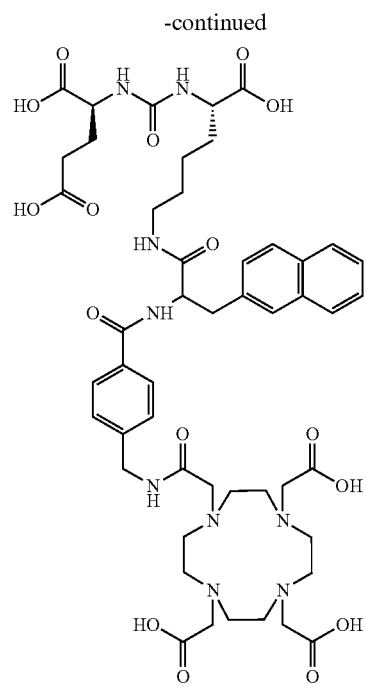
-continued
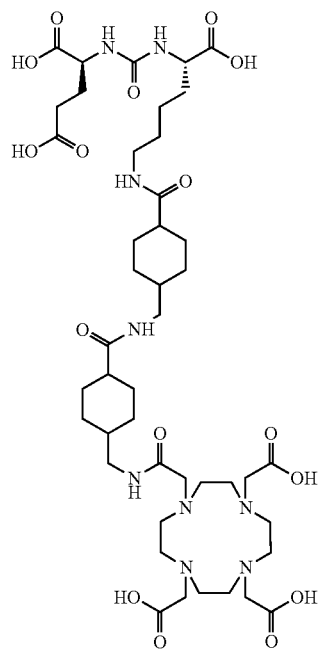
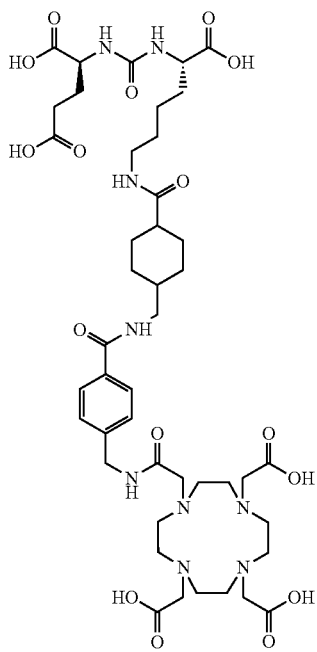
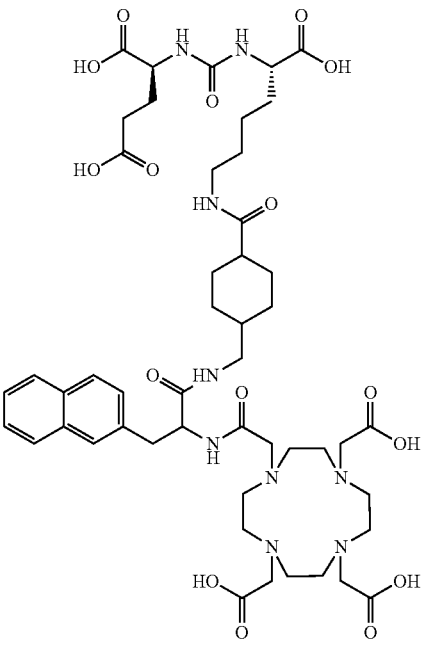
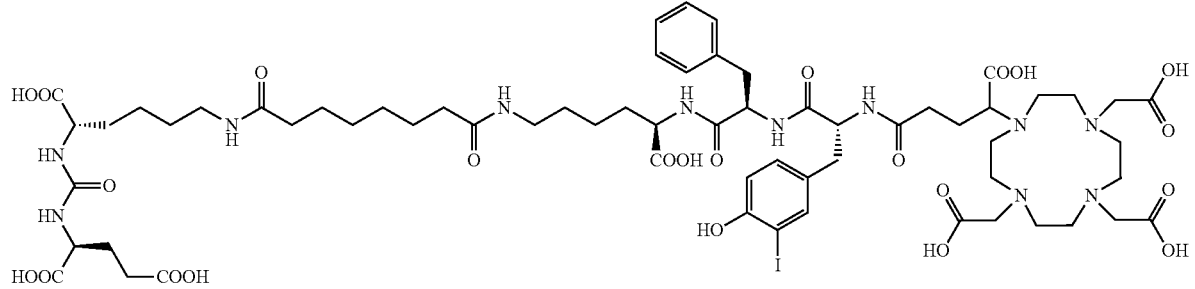

-continued

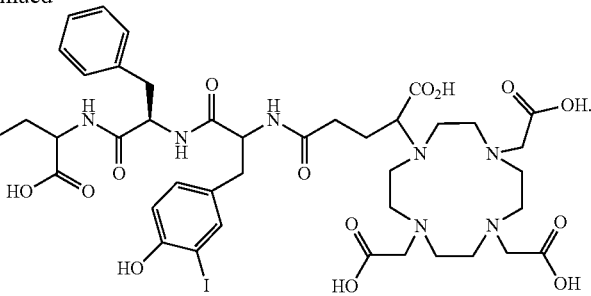

3. The method of claim 1, wherein at least one Ac-225-radiopharmaceutical is Ac-225-PSMA-617, wherein Ac-225-PSMA-617 is a compound according to a formula

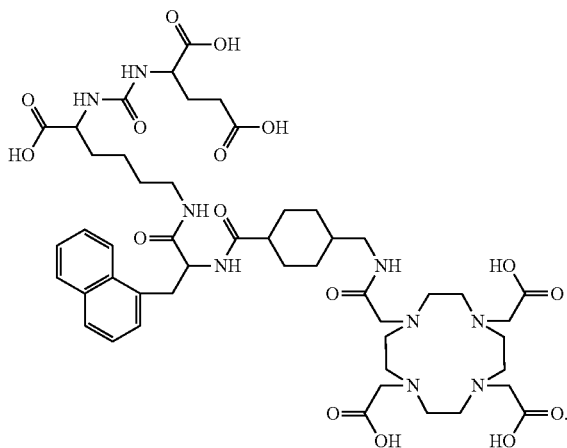 [SMILES: O=C(O)CCC(NC(=O)NC(CCCCNC(=O)C(Cc1cccc2ccccc12)NC(=O)C1CCC(CNC(=O)CN2CCN(CC(=O)O)CCN(CC(=O)O)CCN(CC(=O)O)CC2)CC1)C(=O)O)C(=O)O]

chelating a Ac-225 radionuclide with its 1,4,7,10-tetraazacyclodeodecane-N,N', N'', N'''-tetraacetic acid moiety.

4. The method of claim 1, wherein said PSMA expressing cancers are selected among prostate cancer, conventional renal cell cancers, cancers of the transitional cells of the bladder, testicular-embryonal cancers, neuroendocrine cancers, colon cancers, brain tumors and breast cancers.

5. The method of claim 1, wherein the cancer is a disseminated cancer.

6. The method of claim 4, wherein said PSMA expressing cancer is prostate cancer.

7. The method of claim 4, wherein said PSMA expressing cancer is breast cancer.

8. The method of claim 1, wherein the effective amount of said one or more Ac-225-radiopharmaceuticals is administered as a dosage of from 30 kBq to 250 kBq/kg of body weight.

9. The method of claim 8, wherein the dosage ranges from 50 kBq to 200 kBq/kg of body weight.

10. The method of claim 1, wherein the effective amount of said one or more Ac-225-radiopharmaceuticals is administered as a unitary dosage of from 4 MBq to 25 MBq.

11. The method of claim 10, wherein the unitary dosage ranges from 5 MBq to 20 MBq.

12. The method of claim 8, wherein administering of the effective amount of said one or more Ac-225-radiopharmaceuticals to the patient is repeated after 15 to 90 days.

13. The method of claim 10, wherein administering of the effective amount of said one or more Ac-225-radiopharmaceuticals to the patient is repeated after 15 to 90 days.

\* \* \* \* \*